(12) United States Patent
Robinson et al.

(10) Patent No.: US 9,265,665 B2
(45) Date of Patent: Feb. 23, 2016

(54) INFLATABLE OFF-LOADING WOUND DRESSING ASSEMBLIES, SYSTEMS, AND METHODS

(75) Inventors: Timothy Mark Robinson, Basingstoke (GB); Christopher Brian Locke, Bournemouth (GB); Richard Daniel John Coulthard, Verwood (GB)

(73) Assignee: KCI Licensing, Inc., San Antonio, TX (US)

( * ) Notice: Subject to any disclaimer, the term of this patent is extended or adjusted under 35 U.S.C. 154(b) by 933 days.

(21) Appl. No.: 13/183,280

(22) Filed: Jul. 14, 2011

(65) Prior Publication Data

US 2012/0016323 A1 Jan. 19, 2012

Related U.S. Application Data

(60) Provisional application No. 61/365,614, filed on Jul. 19, 2010, provisional application No. 61/407,194, filed on Oct. 27, 2010, provisional application No. 61/418,730, filed on Dec. 1, 2010.

(51) Int. Cl.
*A61M 1/00* (2006.01)
*A61M 27/00* (2006.01)
*A61F 13/00* (2006.01)
(Continued)

(52) U.S. Cl.
CPC ..... *A61F 13/00055* (2013.01); *A61F 13/00068* (2013.01); *A61F 13/02* (2013.01); *A61M 1/009* (2014.02); *A61M 1/0031* (2013.01); *A61M 1/0088* (2013.01); *A61M 27/00* (2013.01); *G08B 21/20* (2013.01); *A61F 2013/0054* (2013.01); *A61F 2013/00174* (2013.01); *A61F 2013/00421* (2013.01); *A61F 2013/00536* (2013.01); *A61F 2013/00961* (2013.01); *A61M 1/0025* (2014.02); *A61M 2205/3317* (2013.01);
(Continued)

(58) Field of Classification Search
CPC ... A61M 1/00; A61M 1/0008; A61M 1/0088; A61M 27/00; A61M 35/00
USPC ......................................... 604/304, 313, 319
See application file for complete search history.

(56) References Cited

U.S. PATENT DOCUMENTS

| 1,355,846 A | 10/1920 | Rannells |
| 2,547,758 A | 4/1951 | Keeling |

(Continued)

FOREIGN PATENT DOCUMENTS

| AU | 550575 A1 | 8/1982 |
| AU | 745271 | 4/1999 |

(Continued)

OTHER PUBLICATIONS

International Search Report and Written Opinion date mailed Oct. 21, 2011; PCT International Application No. PCT/US2011/044196.
(Continued)

*Primary Examiner* — Melanie Hand

(57) ABSTRACT

To offload forces from a tissue site being treated with reduced pressure, an offloading pressure component may be used as part of a reduced-pressure treatment system. A reduced-pressure source of the reduced-pressure treatment system vents positive pressure exhaust into the offloading pressure component to inflate the offloading pressure component. The offloading pressure component disperses forces away from the tissue site. Other devices, methods, and systems are presented.

26 Claims, 5 Drawing Sheets

(51) Int. Cl.
*G08B 21/20* (2006.01)
*A61F 13/02* (2006.01)

(52) U.S. Cl.
CPC ............... *A61M 2205/3344* (2013.01); *A61M 2205/3592* (2013.01); *A61M 2205/6081* (2013.01)

(56) References Cited

U.S. PATENT DOCUMENTS

| | | | |
|---|---|---|---|
| 2,632,443 A | 3/1953 | Lesher | |
| 2,682,873 A | 7/1954 | Evans et al. | |
| 2,910,763 A | 11/1959 | Lauterbach | |
| 2,969,057 A | 1/1961 | Simmons | |
| 3,066,672 A | 12/1962 | Crosby, Jr. et al. | |
| 3,171,410 A | 3/1965 | Towle | |
| 3,367,332 A | 2/1968 | Groves | |
| 3,520,300 A | 7/1970 | Flower, Jr. | |
| 3,568,675 A | 3/1971 | Harvey | |
| 3,648,692 A | 3/1972 | Wheeler | |
| 3,682,180 A | 8/1972 | McFarlane | |
| 3,826,254 A | 7/1974 | Mellor | |
| 4,080,970 A | 3/1978 | Miller | |
| 4,096,853 A | 6/1978 | Weigand | |
| 4,139,004 A | 2/1979 | Gonzalez, Jr. | |
| 4,165,748 A | 8/1979 | Johnson | |
| 4,184,510 A | 1/1980 | Murry et al. | |
| 4,233,969 A | 11/1980 | Lock et al. | |
| 4,245,630 A | 1/1981 | Lloyd et al. | |
| 4,256,109 A | 3/1981 | Nichols | |
| 4,261,363 A | 4/1981 | Russo | |
| 4,275,721 A | 6/1981 | Olson | |
| 4,284,079 A | 8/1981 | Adair | |
| 4,297,995 A | 11/1981 | Golub | |
| 4,333,468 A | 6/1982 | Geist | |
| 4,373,519 A | 2/1983 | Errede et al. | |
| 4,382,441 A | 5/1983 | Svedman | |
| 4,392,853 A | 7/1983 | Muto | |
| 4,392,858 A | 7/1983 | George et al. | |
| 4,419,097 A | 12/1983 | Rowland | |
| 4,465,485 A | 8/1984 | Kashmer et al. | |
| 4,475,909 A | 10/1984 | Eisenberg | |
| 4,480,638 A | 11/1984 | Schmid | |
| 4,525,166 A | 6/1985 | Leclerc | |
| 4,525,374 A | 6/1985 | Vaillancourt | |
| 4,540,412 A | 9/1985 | Van Overloop | |
| 4,543,100 A | 9/1985 | Brodsky | |
| 4,548,202 A | 10/1985 | Duncan | |
| 4,551,139 A | 11/1985 | Plaas et al. | |
| 4,569,348 A | 2/1986 | Hasslinger | |
| 4,605,399 A | 8/1986 | Weston et al. | |
| 4,608,041 A | 8/1986 | Nielsen | |
| 4,640,688 A | 2/1987 | Hauser | |
| 4,655,754 A | 4/1987 | Richmond et al. | |
| 4,664,662 A | 5/1987 | Webster | |
| 4,710,165 A | 12/1987 | McNeil et al. | |
| 4,733,659 A | 3/1988 | Edenbaum et al. | |
| 4,743,232 A | 5/1988 | Kruger | |
| 4,758,220 A | 7/1988 | Sundblom et al. | |
| 4,787,888 A | 11/1988 | Fox | |
| 4,826,494 A | 5/1989 | Richmond et al. | |
| 4,838,883 A | 6/1989 | Matsuura | |
| 4,840,187 A | 6/1989 | Brazier | |
| 4,863,449 A | 9/1989 | Therriault et al. | |
| 4,872,450 A | 10/1989 | Austad | |
| 4,878,901 A | 11/1989 | Sachse | |
| 4,897,081 A | 1/1990 | Poirier et al. | |
| 4,906,233 A | 3/1990 | Moriuchi et al. | |
| 4,906,240 A | 3/1990 | Reed et al. | |
| 4,919,654 A | 4/1990 | Kalt et al. | |
| 4,941,882 A | 7/1990 | Ward et al. | |
| 4,953,565 A | 9/1990 | Tachibana et al. | |
| 4,969,880 A | 11/1990 | Zamierowski | |
| 4,984,611 A * | 1/1991 | Takatsuki et al. ............... 141/65 | |
| 4,985,019 A | 1/1991 | Michelson | |
| 5,037,397 A | 8/1991 | Kalt et al. | |
| 5,060,339 A * | 10/1991 | Evers ............................... 15/246 |
| 5,086,170 A | 2/1992 | Luheshi et al. | |
| 5,092,858 A | 3/1992 | Benson et al. | |
| 5,100,396 A | 3/1992 | Zamierowski | |
| 5,134,994 A | 8/1992 | Say | |
| 5,149,331 A | 9/1992 | Ferdman et al. | |
| 5,167,613 A | 12/1992 | Karami et al. | |
| 5,176,663 A | 1/1993 | Svedman et al. | |
| 5,215,522 A | 6/1993 | Page et al. | |
| 5,232,453 A | 8/1993 | Plass et al. | |
| 5,261,893 A | 11/1993 | Zamierowski | |
| 5,274,074 A * | 12/1993 | Tang et al. ..................... 528/370 |
| 5,278,100 A | 1/1994 | Doan et al. | |
| 5,279,550 A | 1/1994 | Habib et al. | |
| 5,298,015 A | 3/1994 | Komatsuzaki et al. | |
| 5,342,376 A | 8/1994 | Ruff | |
| 5,344,415 A | 9/1994 | DeBusk et al. | |
| 5,358,494 A | 10/1994 | Svedman | |
| 5,437,622 A | 8/1995 | Carion | |
| 5,437,651 A | 8/1995 | Todd et al. | |
| 5,527,293 A | 6/1996 | Zamierowski | |
| 5,549,584 A | 8/1996 | Gross | |
| 5,556,375 A | 9/1996 | Ewall | |
| 5,607,388 A | 3/1997 | Ewall | |
| 5,636,643 A | 6/1997 | Argenta et al. | |
| 5,645,081 A | 7/1997 | Argenta et al. | |
| 6,071,267 A | 6/2000 | Zamierowski | |
| 6,135,116 A | 10/2000 | Vogel et al. | |
| 6,241,747 B1 | 6/2001 | Ruff | |
| 6,287,316 B1 | 9/2001 | Agarwal et al. | |
| 6,345,623 B1 | 2/2002 | Heaton et al. | |
| 6,488,643 B1 | 12/2002 | Tumey et al. | |
| 6,493,568 B1 | 12/2002 | Bell et al. | |
| 6,553,998 B2 | 4/2003 | Heaton et al. | |
| 6,814,079 B2 | 11/2004 | Heaton et al. | |
| 2002/0077661 A1 | 6/2002 | Saadat | |
| 2002/0115951 A1 | 8/2002 | Norstrem et al. | |
| 2002/0120185 A1 | 8/2002 | Johnson | |
| 2002/0143286 A1 | 10/2002 | Tumey | |
| 2007/0078366 A1* | 4/2007 | Haggstrom et al. ............ 602/53 |
| 2008/0103462 A1 | 5/2008 | Wenzel et al. | |
| 2009/0260639 A1 | 10/2009 | Hsu et al. | |
| 2010/0298792 A1* | 11/2010 | Weston et al. ................ 604/319 |

FOREIGN PATENT DOCUMENTS

| | | |
|---|---|---|
| AU | 755496 | 2/2002 |
| CA | 2005436 | 6/1990 |
| DE | 26 40 413 | 3/1978 |
| DE | 43 06 478 A1 | 9/1994 |
| DE | 295 04 378 U1 | 10/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 B1 | 8/2004 |
| GB | 692578 | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 333 965 A | 8/1999 |
| GB | 2 329 127 B | 8/2000 |
| JP | 4129536 | 4/1992 |
| SG | 71559 | 4/2002 |
| WO | WO 80/02182 | 10/1980 |
| WO | WO 87/04626 | 8/1987 |
| WO | WO 90/10424 | 9/1990 |
| WO | WO 93/09727 | 5/1993 |
| WO | WO 94/20041 | 9/1994 |
| WO | WO 96/05873 | 2/1996 |
| WO | WO 97/18007 | 5/1997 |
| WO | WO 99/13793 | 3/1999 |

(56) References Cited

FOREIGN PATENT DOCUMENTS

WO    WO 2006/114637 A2    11/2006
WO    WO 2009/114624 A2    9/2009

OTHER PUBLICATIONS

N.A. Bagautdinov, "Variant of External Vacuum Aspiration in the Treatment of Purulent Diseases of the Soft Tissues," *Current Problems in Modern Clinical Surgery: Interdepartmental Collection*, edited by V. Ye Volkov et al. (Chuvashia State University, Cheboksary, U.S.S.R. 1986);pp. 94-96 (certified translation).
Louis C. Argenta, MD and Michael J. Morykwas, PhD; "Vacuum-Assisted Closure: A New Method for Wound Control and Treatment: Clinical Experience"; Annals of Plastic Surgery, vol. 38, No. 6, Jun. 1997; pp. 563-576.
Susan Mendez-Eastmen, RN; "When Wounds Won't Heal" RN Jan. 1998, vol. 61(1); Medical Economics Company, Inc., Montvale, NJ, USA; pp. 20-24.
James H. Blackburn, II, MD, et al; "Negative-Pressure Dressings as a Bolster for Skin Grafts"; Annals of Plastic Surgery, vol. 40, No. 5, May 1998, pp. 453-457.
John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.
S.E. Greer, et al "The Use of Subatmospheric Pressure Dressing Therapy to Close Lymphocutaneous Fistulas of the Groin" British Journal of Plastic Surgery (2000), 53, pp. 484-487.
George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.
Orringer, Jay, et al; "Management of Wounds in Patients with Complex Enterocutaneous Fistulas"; Surgery, Gynecology & Obstetrics, Jul. 1987, vol. 165, pp. 79-80.
International Search Report for PCT International Application PCT/GB95/01983; Nov. 23, 1995.
PCT International Search Report for PCT International Application PCT/GB98/02713; Jan. 8, 1999.
PCT Written Opinion; PCT International Application PCT/GB98/02713; Jun. 8, 1999.
PCT International Examination and Search Report, PCT International Application PCT/GB96/02802; Jan. 15, 1998 & Apr. 29, 1997.
PCT Written Opinion, PCT International Application PCT/GB96/02802; Sep. 3, 1997.
Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.
Kostyuchenok, B.M., et al; "Vacuum Treatment in the Surgical Management of Purulent Wounds"; Vestnik Khirurgi, Sep. 1986, pp. 18-21 and 6 page English translation thereof.
Davydov, Yu. A., et al; "Vacuum Therapy in the Treatment of Purulent Lactation Mastitis"; Vestnik Khirurgi, May 14, 1986, pp. 66-70, and 9 page English translation thereof.
Yusupov. Yu. N., et al; "Active Wound Drainage", Vestnik Khirurgi, vol. 138, Issue 4, 1987, and 7 page English translation thereof.
Davydov, Yu. A., et al; "Bacteriological and Cytological Assessment of Vacuum Therapy for Purulent Wounds"; Vestnik Khirurgi, Oct. 1988, pp. 48-52, and 8 page English translation thereof.
Davydov, Yu. A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.
Chariker, Mark E., M.D., et al; "Effective Management of incisional and cutaneous fistulae with closed suction wound drainage"; Contemporary Surgery, vol. 34, Jun. 1989, pp. 59-63.
Egnell Minor, Instruction Book, First Edition, 300 7502, Feb. 1975, pp. 24.
Egnell Minor: Addition to the Users Manual Concerning Overflow Protection—Concerns all Egnell Pumps, Feb. 3, 1983, pp. 2.
Svedman, P.: "Irrigation Treatment of Leg Ulcers", The Lancet, Sep. 3, 1983, p. 532-534.
Chinn, Steven D. et al.: "Closed Wound Suction Drainage", The Journal of Foot Surgery, vol. 24, No. 1, 1985, pp. 76-81.
Arnljots, Björn et al.: "Irrigation Treatment in Split-Thickness Skin Grafting of Intractable Leg Ulcers", Scand J. Plast Reconstr. Surg., No. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al.: "A Dressing System Providing Fluid Supply and Suction Drainage Used for Continuous or Intermittent Irrigation", Annals of Plastic Surgery, vol. 17, No. 2, Aug. 1986, pp. 125-133.
K.F. Jeter, T.E. Tintle, and M. Chariker, "Managing Draining Wounds and Fistulae: New and Established Methods," *Chronic Wound Care*, edited by D. Krasner (Health Management Publications, Inc., King of Prussia, PA 1990), pp. 240-246.
G. Živadinović, V. Đukić, Ž.Maksimović, Đ. Radak, and P. Peška, "Vacuum Therapy in the Treatment of Peripheral Blood Vessels," *Timok Medical Journal* 11 (1986), pp. 161-164 (certified translation).
F.E. Johnson, "An Improved Technique for Skin Graft Placement Using a Suction Drain," *Surgery, Gynecology, and Obstetrics* 159 (1984), pp. 584-585.
A.A. Safronov, Dissertation Abstract, *Vacuum Therapy of Trophic Ulcers of the Lower Leg with Simultaneous Autoplasty of the Skin* (Central Scientific Research Institute of Traumatology and Orthopedics, Moscow, U.S.S.R. 1967) (certified translation).
M. Schein, R. Saadia, J.R. Jamieson, and G.A.G. Decker, "The 'Sandwich Technique' in the Management of the Open Abdomen," *British Journal of Surgery* 73 (1986), pp. 369-370.
D.E. Tribble, An Improved Sump Drain-Irrigation Device of Simple Construction, *Archives of Surgery* 105 (1972) pp. 511-513.
M.J. Morykwas, L.C. Argenta, E.I. Shelton-Brown, and W. McGuirt, "Vacuum-Assisted Closure: A New Method for Wound Control and Treatment: Animal Studies and Basic Foundation," *Annals of Plastic Surgery* 38 (1997), pp. 553-562 (Morykwas I).
C.E. Tennants, "The Use of Hypermia in the Postoperative Treatment of Lesions of the Extremities and Thorax, " *Journal of the American Medical Association* 64 (1915), pp. 1548-1549.
Selections from W. Meyer and V. Schmieden, *Bier's Hyperemic Treatment in Surgery, Medicine, and the Specialties: A Manual of Its Practical Application*, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N.A. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").
V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
V.A.C. ® Therapy Clinical Guidelines: A Reference Source for Clinicians (Jul. 2007).

* cited by examiner

INFLATABLE OFF-LOADING WOUND DRESSING ASSEMBLIES, SYSTEMS, AND METHODS

RELATED APPLICATIONS

The present invention claims the benefit, under 35 USC §119(e), of the filing of U.S. Provisional Patent Application Ser. No. 61/365,614, entitled "Inflatable Off-loading Wound Dressing Assemblies, Systems, and Methods," filed 19 Jul. 2010, which is incorporated herein by reference for all purposes; U.S. Provisional Patent Application Ser. No. 61/407,194, entitled "System and Methods For Electrically Detecting The Presence of Exudate In Reduced-Pressure Dressings," filed 27 Oct. 2010, which is incorporated herein by reference for all purposes; and U.S. Provisional Patent Application Ser. No. 61/418,730, entitled "Systems and Methods for Electrically Detecting the Presence of Exudate in Dressings," filed 1 Dec. 2010, which is incorporated herein by reference for all purposes.

FIELD

The disclosure relates generally to reduced-pressure medical treatment systems and more particularly, but not by way of limitation, to inflatable off-loading wound dressing assemblies, systems, and methods.

BACKGROUND

Clinical studies and practice have shown that providing a reduced pressure in proximity to a tissue site augments and accelerates the growth of new tissue at the tissue site. The applications of this phenomenon are numerous, but one particular application of reduced pressure involves treating wounds. This treatment (frequently referred to in the medical community as "negative pressure wound therapy," "reduced-pressure therapy," or "vacuum therapy") provides a number of benefits, including migration of epithelial and subcutaneous tissues, improved blood flow, and micro-deformation of tissue at the wound site. Together these benefits result in increased development of granulation tissue and faster healing times. Typically, reduced pressure is applied by a reduced-pressure source to tissue through a porous pad or other manifold device. In many instances, wound exudate and other liquids from the tissue site are collected within a canister to prevent the liquids from reaching the reduced-pressure source. At times, the tissue site being treated is at a pressure point on the patient, e.g., on the back of a bed-ridden patient.

SUMMARY

In one illustrative embodiment, a reduced-pressure treatment system for applying reduced pressure treatment to a tissue site includes a wound cover for covering the tissue site and forming a sealed space and includes a reduced-pressure source that provides reduced pressure to the tissue site and provides a positive pressure exhaust. The reduced-pressure treatment system further includes an offloading pressure component for dispersing positive pressure exerted on or near the tissue site. The offloading pressure component is fluidly coupled to the reduced-pressure source for receiving at least a portion of the positive pressure exhaust.

According to another illustrative embodiment, a system for treating a tissue site with reduced pressure includes a reduced-pressure source that produces reduced pressure and a positive pressure exhaust and includes an offloading pressure component. The offloading pressure component has a deflated state and an inflated state. The offloading pressure component includes at least one flexible wall forming an inner space of the offloading pressure component. The inner space is fluidly coupled to the reduced-pressure source and is operable to receive the positive pressure exhaust generated by the reduced-pressure source.

In yet another illustrative embodiment, a method for offloading pressure exerted proximate to a tissue site to which reduced pressure is applied includes applying a wound cover over the tissue site. The method further includes applying reduced pressure to the tissue site using a reduced-pressure source coupled to the wound cover. The method further includes inflating an inner space of an offloading pressure component coupled to the reduced-pressure source. The offloading pressure component is operable to disperse positive pressure exerted proximate to the tissue site.

Other features and advantages of the illustrative embodiments will become apparent with reference to the drawings and detailed description that follow.

DETAILED DESCRIPTION OF ILLUSTRATIVE EMBODIMENTS

In the following detailed description of several illustrative embodiments, reference is made to the accompanying drawings that form a part hereof, and in which is shown by way of illustration specific preferred embodiments in which the invention may be practiced. These embodiments are described in sufficient detail to enable those skilled in the art to practice the invention, and it is understood that other embodiments may be utilized and that logical structural, mechanical, electrical, and chemical changes may be made without departing from the spirit or scope of the invention. To avoid detail not necessary to enable those skilled in the art to practice the embodiments described herein, the description may omit certain information known to those skilled in the art. The following detailed description is, therefore, not to be taken in a limiting sense, and the scope of the illustrative embodiments are defined only by the appended claims.

Figure 1:
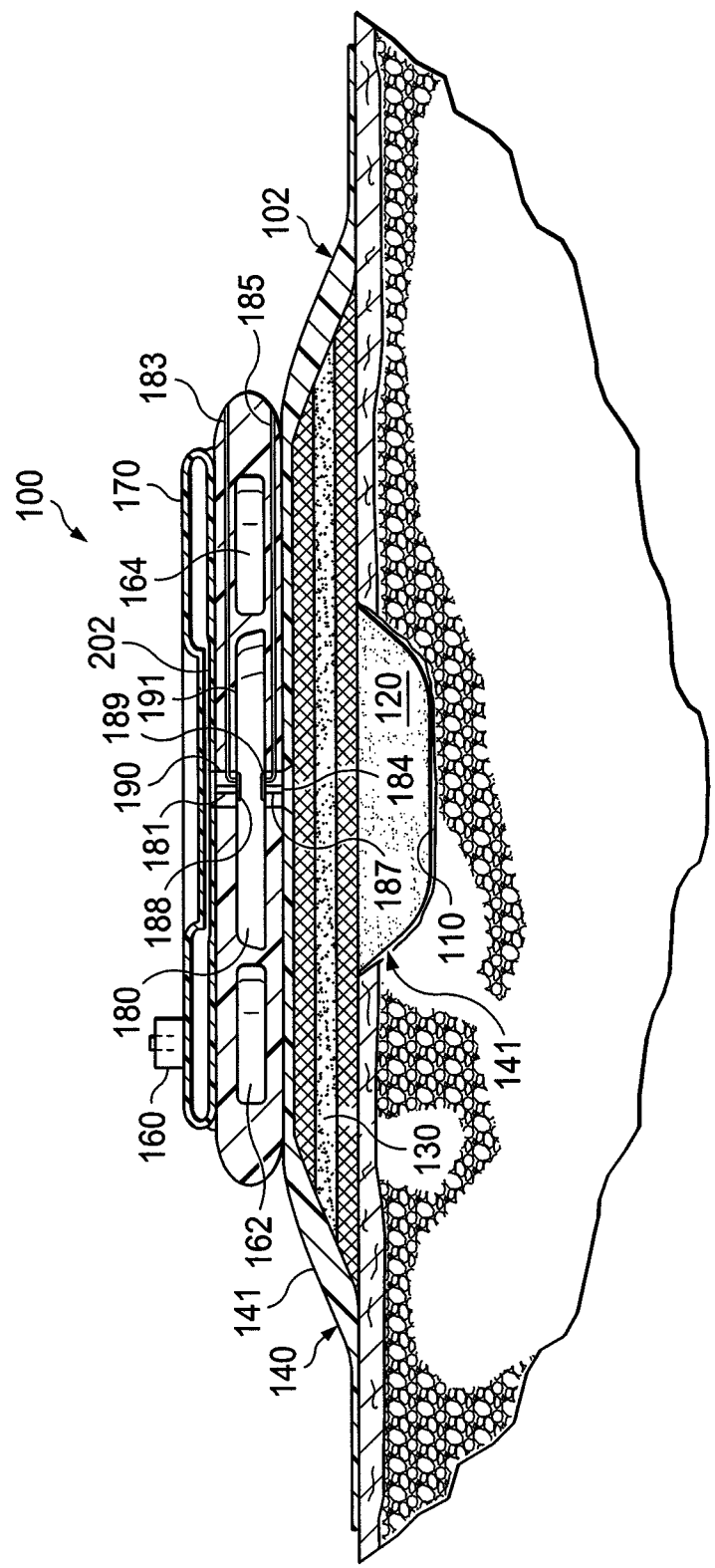
FIG. 1 is a schematic, cross-sectional side view of a reduced-pressure treatment system having an offloading pressure component according to an illustrative embodiment shown in a deflated state.

Referring to the drawings and initially and primarily to FIG. 1, a cross-sectional side view of a reduced-pressure treatment system 100 according to an illustrative embodiment is presented. The reduced-pressure treatment system 100 is applied to a tissue site 110, such as a wound. The tissue site may be a wound or defect located on or within any tissue, including but not limited to, bone tissue, adipose tissue, muscle tissue, neural tissue, dermal tissue, vascular tissue, connective tissue, cartilage, tendons, or ligaments. The tissue site may further refer to areas of any tissue that are not necessarily wounded or defective, but are instead areas in which it is desired to add or promote the growth of additional tissue. For example, reduced pressure tissue treatment may be used in certain tissue areas to grow additional tissue that may be harvested and transplanted to another tissue location.

The reduced-pressure treatment system 100 includes a dressing assembly 102 and a reduced-pressure source 180, which may be integral to or separate from the dressing assembly 102. The dressing assembly 102 of the illustrative embodiment of FIG. 1 includes a cover 140, the reduced-pressure source 180 coupled to or incorporated into the cover 140 for providing reduced pressure treatment to the tissue site 110, and an absorbent layer 130 for absorbing exudates and other liquids drawn from the tissue site 110. The reduced-pressure treatment system 100 includes an offloading pressure component 170 for dispersing positive pressure exerted on or near the tissue site 110. The offloading pressure component 170 may, for example, allow a patient to lay on their back even though the tissue site being treated is on their back because the offloading pressure component 170 offloads or prevents a substantial load from being placed on the tissue site 110. The offloading pressure component 170 is an inflatable bladder or inflatable and deflatable bladder.

In addition, in certain embodiments, the reduced-pressure treatment system 100 may include an onboard control unit 164, an internal power source, such as a battery 162, and one or more sensors (not shown), such as, but not limited to, a pressure sensor for monitoring a pressure level exerted by the reduced-pressure source 180 on the tissue site 110, or for monitoring a pressure level within the offloading pressure component 170. As used herein "or" does not require mutual exclusivity. The one or more sensors may provide pressure readings to the onboard control unit 164 or an external reduced-pressure treatment unit for enabling the onboard control unit 164 to adjust the operations of the reduced-pressure treatment system 100.

The cover 140, or drape, may be made of a flexible material that covers the tissue site 110 to protect the tissue site 110 from the external environment and forms or helps form a fluid seal. The cover 140 may extend beyond a perimeter of the tissue site 110 and may include an adhesive, bonding agent, or other attachment device on a peripheral portion of the cover 140 to secure the cover 140 to tissue adjacent to the tissue site 110. The cover 140 may be used to create a sealed space 141 over the tissue site 110. The adhesive disposed on the cover 140 may be used to form a fluid seal between the tissue and the cover 140 to prevent leakage of reduced pressure from the tissue site 110.

The absorbent layer 130 is disposed beneath (for the orientation shown) the cover 140 and is used to absorb exudates and other liquids drawn from the tissue site 110. The absorbent layer 130 may be integrated with the cover 140 or the absorbent layer 130 may be a separate component of the reduced-pressure treatment system 100. The absorbent layer 130 may be made from any material capable of absorbing liquid, such as exudate, from the tissue site 110. In one illustrative embodiment, the absorbent layer 130 is made from a super absorbent fiber. The super absorbent fibers may hold onto or bond to the liquid in conjunction with a physical or chemical change to the fibers. In one illustrative, non-limiting example, the super absorbent fiber may include the Super Absorbent Fiber (SAF) material from Technical Absorbents®, Ltd. In some embodiments, the absorbent layer 130 may include an odor adsorption material (not shown) such as, but not limited to, activated charcoal for reducing or eliminating the odor associated with the collected exudates.

The reduced-pressure treatment system 100 may also include a treatment manifold 120 adapted to be positioned proximate to the tissue site 110. The treatment manifold 120 may be partially or fully in contact with the tissue site 110 that is being treated by the reduced-pressure treatment system 100. When the tissue site 110 is a wound, the treatment manifold 120 may partially or fully fill the wound bed. The treatment manifold 120 may be any size, shape, or thickness depending on a variety of factors, such as the type of treatment being implemented or the nature and size of the tissue site 110. For example, the size and shape of the treatment manifold 120 may be customized by a user to cover a particular portion of the tissue site 110, or to fill or partially fill the tissue site 110. The treatment manifold 120 may have, for example, a square shape, or may be shaped as a circle, oval, polygon, an irregular shape, or any other shape.

The treatment manifold 120 is a material, e.g., a foam material, that distributes reduced pressure to the tissue site 110 when the treatment manifold 120 is in contact with or near the tissue site 110. The foam material may be either hydrophobic or hydrophilic. In one illustrative, non-limiting example, the treatment manifold 120 is an open-cell, reticulated polyurethane foam, such as GranuFoam® dressing available from Kinetic Concepts, Inc. of San Antonio, Tex.

In the example in which the treatment manifold 120 is made from a hydrophilic material, the treatment manifold 120 also functions to wick fluid away from the tissue site 110, while continuing to provide reduced pressure to the tissue site 110 as a manifold. The wicking properties of the treatment manifold 120 draw fluid away from the tissue site 110 by capillary flow or other wicking mechanisms. An example of a hydrophilic foam is a polyvinyl alcohol, open-cell foam, such as V.A.C. WhiteFoam® dressing available from Kinetic Concepts, Inc. of San Antonio, Tex. Other hydrophilic foams may include those made from polyether. Other foams that may exhibit hydrophilic characteristics include hydrophobic foams that have been treated or coated to provide hydrophilicity.

The treatment manifold 120 may be constructed from bioresorbable materials that do not have to be removed from a patient's body following use of the reduced-pressure dressing assembly 102. Suitable bioresorbable materials may include, without limitation, a polymeric blend of polylactic acid (PLA) and polyglycolic acid (PGA). The polymeric blend may also include, without limitation, polycarbonates, polyfumarates, and capralactones. The treatment manifold 120 may further serve as a scaffold for new cell-growth, or a scaffold material may be used in conjunction with the treatment manifold 120 to promote cell-growth. A scaffold is a substance or structure used to enhance or promote the growth of cells or formation of tissue, such as a three-dimensional porous structure that provides a template for cell growth. Illustrative examples of scaffold materials include calcium phosphate, collagen, PLA/PGA, coral hydroxy apatites, carbonates, or processed allograft materials.

In the illustrative embodiment of FIG. 1, reduced pressure is applied to the tissue site 110 by the reduced-pressure source 180. In one embodiment, the reduced-pressure source 180 is a micropump 191 that may be, for example, an electrically-driven vacuum pump and in other embodiments may be a non-motor driven pump. In still other illustrative embodiments, the reduced-pressure source 180 may be remote but fluidly coupled to the dressing assembly 102. In such embodiments, a dual lumen conduit may be used with one lumen delivering reduced pressure to the tissue site and one lumen delivering positive pressure to the inflatable portions, e.g., the offloading pressure component 170.

The micropump 191 may be a micropump that is small and light enough that the cover 140 is able to be maintained on the tissue site 110 with the micropump 191 included. Furthermore, the size and weight of the micropump 191 should be such that the cover 140 does not pull or otherwise adversely affect the tissue site 110. In one embodiment, the micropump 191 may be a disk pump having a piezoelectric actuator. In this and other non-motor-driven pump embodiments, the pump used to generate reduced pressure is not driven by an electric motor or other motor. In the case of the piezoelectric pump, the pump generates fluid flow by supplying an electric current to a piezoelectric actuator. The piezoelectric actuator vibrates when supplied with electric current, and these vibrations are used to generate a pressure differential within a pump cavity (relative to the ambient environment of the pump). The piezoelectric actuator may be positioned directly adjacent to the pump cavity such that the vibration of the actuator is directly transformed into pressure waves within the pump cavity, or alternatively the piezoelectric actuator may be positioned adjacent a diaphragm that transmits the vibrations of the piezoelectric actuator to the pump cavity. In an alternative embodiment, the micropump 191 may be a peristaltic pump that is used for pumping a variety of fluids. It should be understood that alternative pump technologies may also be utilized and that rotary, linear, or other configurations of pumps may be utilized. In still another embodiment, reduced pressure may be supplied from a location remote from the cover 140.

In another illustrative embodiment, the reduced-pressure source 180 may instead be a manually-actuated or manually-charged pump that does not require electrical power. In one embodiment, the reduced-pressure source 180 may be integrated as part of the cover 140. The reduced-pressure source 180 supplies reduced pressure to the tissue site 110 and draws exudates and other liquids from the tissue site 110, through the treatment manifold 120 and into the absorbent layer 130.

Reduced pressure generally refers to a pressure less than the ambient pressure at a tissue site that is being subjected to treatment. In most cases, this reduced pressure will be less than the atmospheric pressure at which the patient is located. Alternatively, the reduced pressure may be less than a hydrostatic pressure associated with tissue at the tissue site 110. Reduced pressure may initially generate fluid flow in the area of the tissue site 110. As the hydrostatic pressure around the tissue site 110 approaches the desired reduced pressure, the flow may subside, and the reduced pressure is then maintained. Unless otherwise indicated, values of pressure stated herein are gauge pressures. Similarly, references to increases in reduced pressure typically refer to a decrease in absolute pressure, while decreases in reduced pressure typically refer to an increase in absolute pressure.

In the illustrative embodiment of FIG. 1, the reduced-pressure source 180 includes an exhaust port 190 for exhausting gas (positive pressure exhaust) generated during operation of the reduced-pressure source 180. The gas exhausted through the exhaust port 190 is used to inflate the offloading pressure component 170, which may comprise an inflatable bladder. In some embodiments, the reduced-pressure source 180 may include an exhaust valve 188 for controlling or limiting the flow of the gas exhausted by the reduced-pressure source 180. For instance, in one embodiment, the exhaust valve 188 is operable to control or limit exhaust gas flow through either an exhaust port path 181 leading out of exhaust port 190 to the inflatable device 170 or to an atmospheric exhaust path 183 that directs the gas exhausted from the reduced-pressure source 180 to enter the surrounding atmosphere or be delivered to another location. While not explicitly shown, the atmospheric exhaust path 183 may include an odor filter, e.g., a charcoal filter (see, e.g., charcoal filter 244 in FIG. 6). The flow may be continuous or intermittent.

For example, the exhaust valve 188, or positive-pressure valve, may be configured to exhaust all or a portion of the gas through the atmospheric exhaust path 183 if the offloading pressure component 170 is to remain in a deflated or a semi-deflated state or is already inflated. In one embodiment, the operation of the exhaust valve 188 may be controlled automatically by the onboard control unit 164 or by an external control unit. For example, the onboard control unit 164 may store a set of preconfigured parameters, such as, but not limited to, the desired pressure, frequency of inflation, and the duration of inflation. In addition, or in lieu of, in some embodiments, the operation of the exhaust valve 188 may be manually controlled by a caregiver or a patient by either manually toggling a switch or by the push of a button on a control unit.

In one illustrative embodiment, the positive pressure exhaust from the reduced-pressure source 180 is delivered to the exhaust valve 188 at an inlet. The valve may contain a pressure regulator that provides a safety overpressure release. In other words, if the pressure experienced by the overpressure release is beyond a threshold, the overpressure release will allow fluid to exit. Downstream of the overpressure release may be a (1) manual input valve for bleeding or directing all or a portion of the positive pressure to atmosphere 183 or (2) an automated input that will release positive pressure beyond a threshold.

In addition, in some embodiments, the reduced-pressure source 180 may include a reduced-pressure valve 189, or purge valve, disposed adjacent to a gas inlet 184 of the reduced-pressure source 180. The reduced-pressure valve 189 may be used to redirect, control, or limit the flow of reduced pressure to either an atmospheric reduced-pressure path 185 for receiving airflow from the surrounding atmosphere, or to a tissue site reduced-pressure path 187 for providing reduced pressure to the tissue site 110. For example, in one embodiment, the reduced-pressure source 180 is operable to draw air from the surrounding atmosphere using the reduced-pressure valve 189, and exhaust the drawn air through the exhaust port 190 to quickly inflate the offloading pressure component 170. Alternatively, or in addition to, in some embodiments, the reduced-pressure source 180 is operable to draw air from the surrounding atmosphere, in conjunction with simultaneously providing reduced pressure to the tissue site 110, for inflating the offloading pressure component 170, such as when the reduced pressure being applied to the tissue site 110 is insufficient to produce enough exhaust for inflating the offloading pressure component 170 by itself or as quickly as desired.

In one embodiment, a liquid-air separator (not shown) is positioned between the absorbent layer 130 and the gas inlet 184 that prevents liquid from entering the reduced-pressure source 180 and allows gas (e.g., reduced pressure) to be communicated for maintaining reduced pressure at the tissue site 110. The liquid-air separator may be a hydrophobic or oleophobic filter that prevents passage of liquids, but allows gaseous communication. Examples of a suitable hydrophobic material include an expanded PTFE laminate, such as a hydrophobic medical membrane manufactured by WL Gore & Associates, Newark, Del. In one illustrative embodiment, the PTFE laminate may be a laminate and may have a 1.0 micron reference pore size on non-woven polyester with a thickness range of 0.0068 mm-0.0135 min. An example of a suitable oleophobic material includes an oleophobic expanded ptfe membrane having a 1.0 micron reference pore size on non-woven polyester with a thickness range of 0.15 mm-0.39 mm. The oleophobic membrane may have a minimum air flow of 12 LPM/cm2/bar (15 PSI) and a minimum water entry pressure of 0.8 bar (12.0 PSI). Alternatively, the substantially planar liquid-air separator may be a gravity-based barrier system, or a device that includes a hydrophilic surface to encourage condensation or other separation of liquid from a fluid stream when the fluid stream passes over the surface. Other examples of the liquid-air separator may include sintered metals, sintered nylons, or any other material or device that is capable of separating liquid from a fluid stream, or that is otherwise capable of substantially preventing the passage of liquid while allowing the passage of gases.

Figure 2:
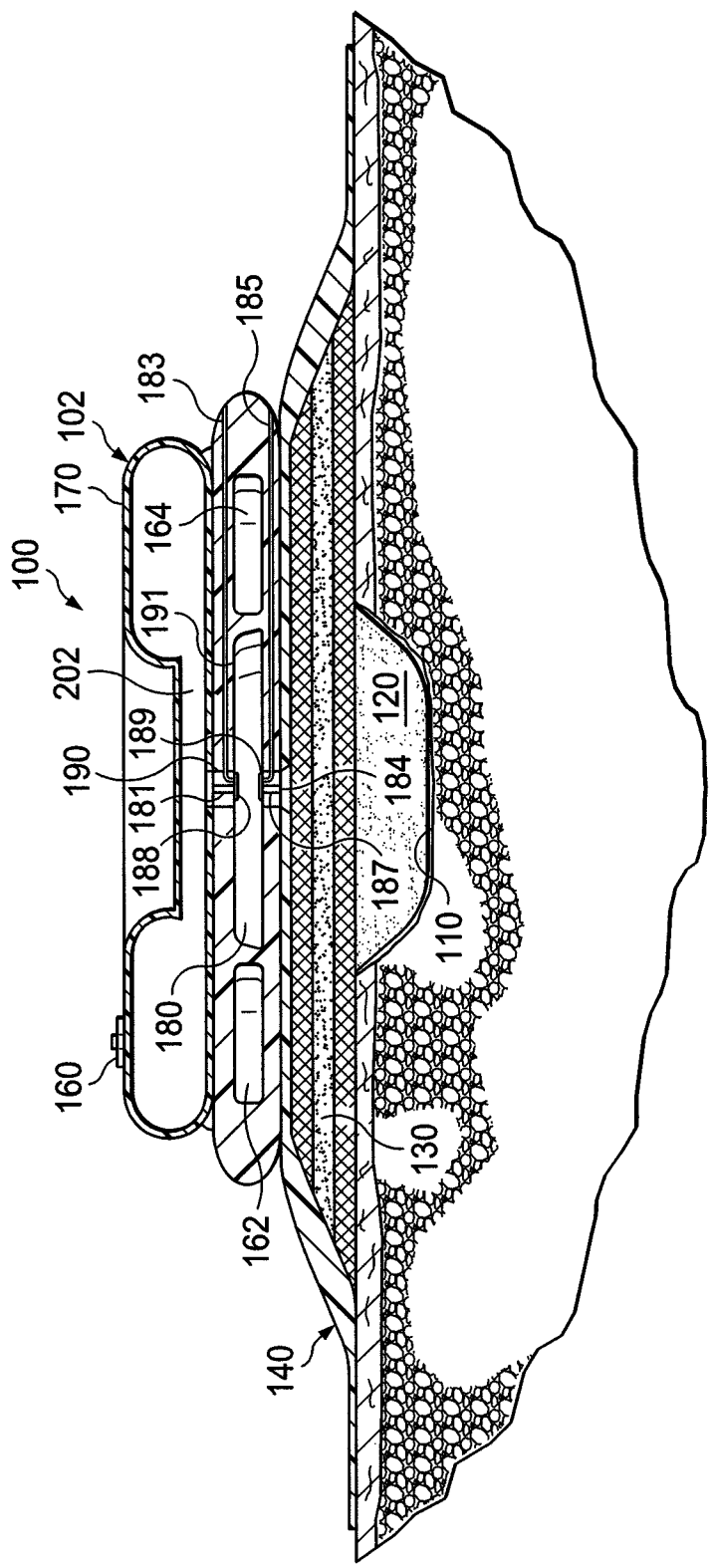
FIG. 2 is a schematic, cross-sectional side view of the reduced-pressure treatment system of FIG. 1 in which the offloading pressure component is in an inflated state according to an illustrative embodiment.

With reference now primarily to FIGS. 1-2, in accordance with a disclosed illustrative embodiment, the offloading pressure component 170 is coupled to the cover 140 and the reduced-pressure source 180, and is operable to receive the exhaust port 190 of the reduced-pressure source 180 through an aperture 178 (FIG. 4) of the offloading pressure component 170. As described above, in one embodiment, positive pressure exhaust generated during operation of the reduced-pressure source 180 exits through the exhaust port 190 and into an inner space 202 of the offloading pressure component 170 and inflates the offloading pressure component 170. FIG. 1 shows the offloading pressure component 170 in a deflated state and FIG. 2 shows the offloading pressure component 170 in the inflated state.

In the depicted embodiment, the offloading pressure component 170 includes a relief valve 160 that is operable to release air from the offloading pressure component 170. In one embodiment, the relief valve 160 may be configured to prevent the pressure from exceeding a maximum predetermined value within the offloading pressure component 170 or may be used to prevent the offloading pressure component 170 from bursting if too much air or pressure is exerted within the offloading pressure component 170. In one illustrative embodiment, the relief valve 160 includes a spring holding the relief valve 160 closed. When the internal pressure exceeds the force of the spring, the relief valve 160 opens and air is released from the offloading pressure component 170 until the pressure drops below the force exerted by the spring. In some embodiments, a user may manually open the relief valve 160 for deflating the offloading pressure component 170. Additionally or alternatively, the relief valve 160 may be automatically controlled by the onboard control unit 164 or by an external control unit for maintaining a desired pressure or state within the offloading pressure component 170.

In one illustrative embodiment, the offloading pressure component 170 forms an annular or donut shape. An interior region of the donut shaped, offloading pressure component 170 may substantially encompass the tissue site 110 for enabling the inflated offloading pressure component 170 to offload pressure to the external boundaries or beyond of the tissue site 110. The offloading pressure component 170 may be circular, oval, square, triangular, or any other desired shape that best conforms to the size and shape of the tissue site 110.

Figure 3:
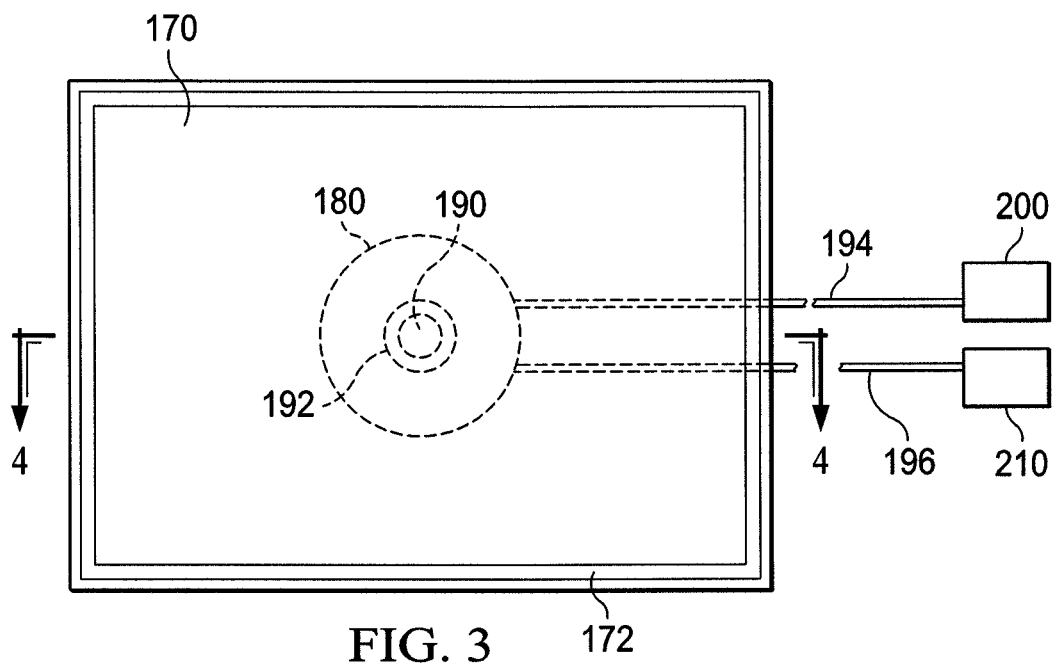
FIG. 3 is a schematic, top view of a reduced-pressure treatment system having an offloading pressure component according to another illustrative embodiment.
Figure 4:
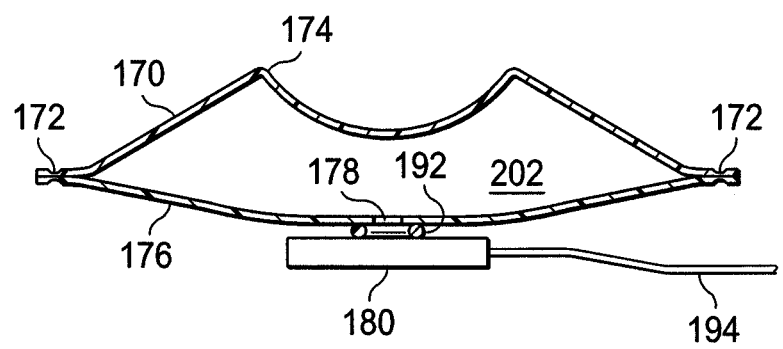
FIG. 4 is a schematic, cross-sectional view of the offloading pressure component of FIG. 3 taken along line 4-4.

Referring now primarily to FIG. 3-4, another illustrative embodiment of the offloading pressure component 170 is presented. This embodiment illustrates the offloading pressure component 170 having a rectangular shape in plan view. The embodiment is shown in a deflated state in FIG. 3. FIG. 4 presents the offloading pressure component 170 of FIG. 3 as a cross section in an inflated state. The cross section of the offloading pressure component 170 shows a concave pillow shape to the offloading pressure component 170. The reduced-pressure source 180 is illustrated beneath (for the orientation shown) the offloading pressure component 170. The offloading pressure component 170 includes an aperture 178 (shown in FIG. 4) that is in fluid communication with the exhaust port 190 of the reduced-pressure source 180. In some embodiments, a sealing ring 192, such as an O-ring, is seated between the exhaust port 190 of the reduced-pressure source 180 and the aperture 178 of the offloading pressure component 170. The sealing ring 192 is operable to maintain a seal that enables gaseous communication between the exhaust port 190 and the aperture 178 of the offloading pressure component 170.

In one illustrative embodiment, the sealing ring 192 may be coupled to both the exhaust port 190 and the offloading pressure component 170 for maintaining a fluid seal. The coupling may be made by any technique, e.g., welding (ultrasonic or RF or other weld), bonding, adhesives, or cements. As another approach to coupling, the bottom layer 176 of the offloading pressure component 170, which may be formed from a transparent material, may be melted with a laser to the sealing ring 192. In another illustrative embodiment, the bottom layer 176 of the offloading pressure component 170 is coupled to the sealing ring 192 and then top layer 174 is coupled to the bottom layer 176.

In another illustrative embodiment, the offloading pressure component 170 may be formed with an inflatable spigot (not shown) that engages the sealing ring 192. The inflatable spigot, which may receive positive pressure exhaust from the reduced-pressure source 180, is like a shaft in an o-ring. As the inflatable spigot inflates or experiences more internal pressure, the strength of the seal between the spigot and sealing ring 192 increases. In still another illustrative embodiment, the top layer 174 of the offloading pressure component 170 is formed from a material not affected by heat from ultrasonic welding and the bottom layer 176 is formed from a material that is affected by heat from ultrasonic welding. The offloading pressure component 170 may placed adjacent to the sealing ring 192 with the bottom layer 176 adjacent to the sealing ring 192 and then exposed to the ultrasonic welding process. Thus, the sealing ring 192 is coupled to the bottom layer 176.

In the depicted embodiment of FIG. 3, the reduced-pressure source 180 includes electrical lead lines 194 for receiving power from an external power source 200. In one embodiment, the reduced-pressure source 180 may also include data lines 196 for communicating data signals between the reduced-pressure source 180 and an external control unit 210. The external control unit 210 may contain sensors, processing units, alarm indicators, memory, databases, software, display units, and a user interface that further facilitate the application of reduced pressure treatment to the tissue site 110. In one example, a sensor or switch (not shown) may be disposed at or near the reduced-pressure source 180 to determine a source pressure generated by the reduced-pressure source 180 or a pressure within the offloading pressure component 170. The sensor may communicate with a processing unit in the external control unit 210 that monitors and controls the reduced pressure that is delivered by the reduced-pressure source 180 or the pressure within the offloading pressure component 170. In one embodiment, an alarm may be triggered in response to the pressure exceeding a threshold, such as, but not limited to, a maximum pressure threshold or a minimum pressure threshold.

Referring primarily to FIG. 4, in one embodiment, the offloading pressure component 170 comprises a top layer 174

(or first layer) and a bottom layer 176 (or second layer). The top layer 174 and the bottom layer 176 may be made of any type of flexible film material such as, but not limited to, plastic or rubber. In some embodiments, the top layer 174 and the bottom layer 176 may be made of different materials. The top layer 174 and the bottom layer 176 may be coupled together by any suitable means, such as, but not limited to, welding or adhesively bonding the two layers together, or formed as an integral member. For example, FIGS. 3 and 4 depict weld lines 172 that connect the top layer 174 and the bottom layer 176 together. The top layer 174 and the bottom layer 176 form the inner space 202 that is operable to receive air from an exhaust port 190 through an aperture 178 located on the bottom layer 176. The top layer 174 may be formed with a concave area that is over the tissue site being treated.

Although FIG. 4 depicts an embodiment comprising of two layers, in alternative embodiments, the offloading pressure component 170 may comprise any number of layers. For example, in one embodiment, the offloading pressure component 170 may comprise a single layer that is sealed directly to the cover 140 to create the inner space 202 between the single layer and the cover 140. In other embodiments, the offloading pressure component 170 may comprise more than two layers. For example, in one embodiment, the offloading pressure component 170 may have multiple layers between the top layer 174 and the bottom layer 176 for creating a stack of cushioned air within the inner space 202, or a cushion within a cushion.

Figure 5:
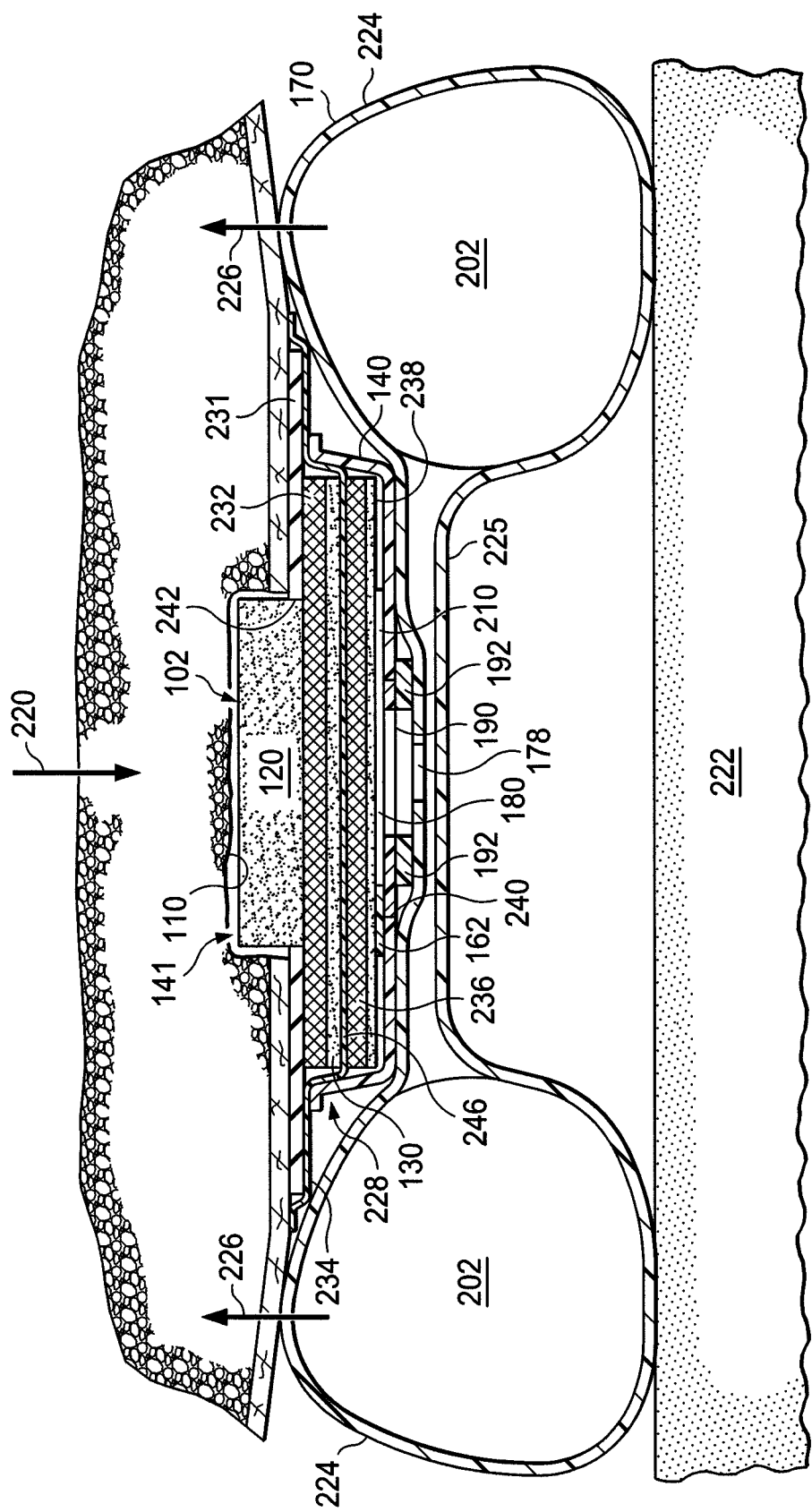
FIG. 5 is a schematic, cross-sectional view of an illustrative embodiment of a reduced-pressure treatment system shown with an inflated offloading pressure component dispersing a force exerted by a patient's weight.
Figure 6:
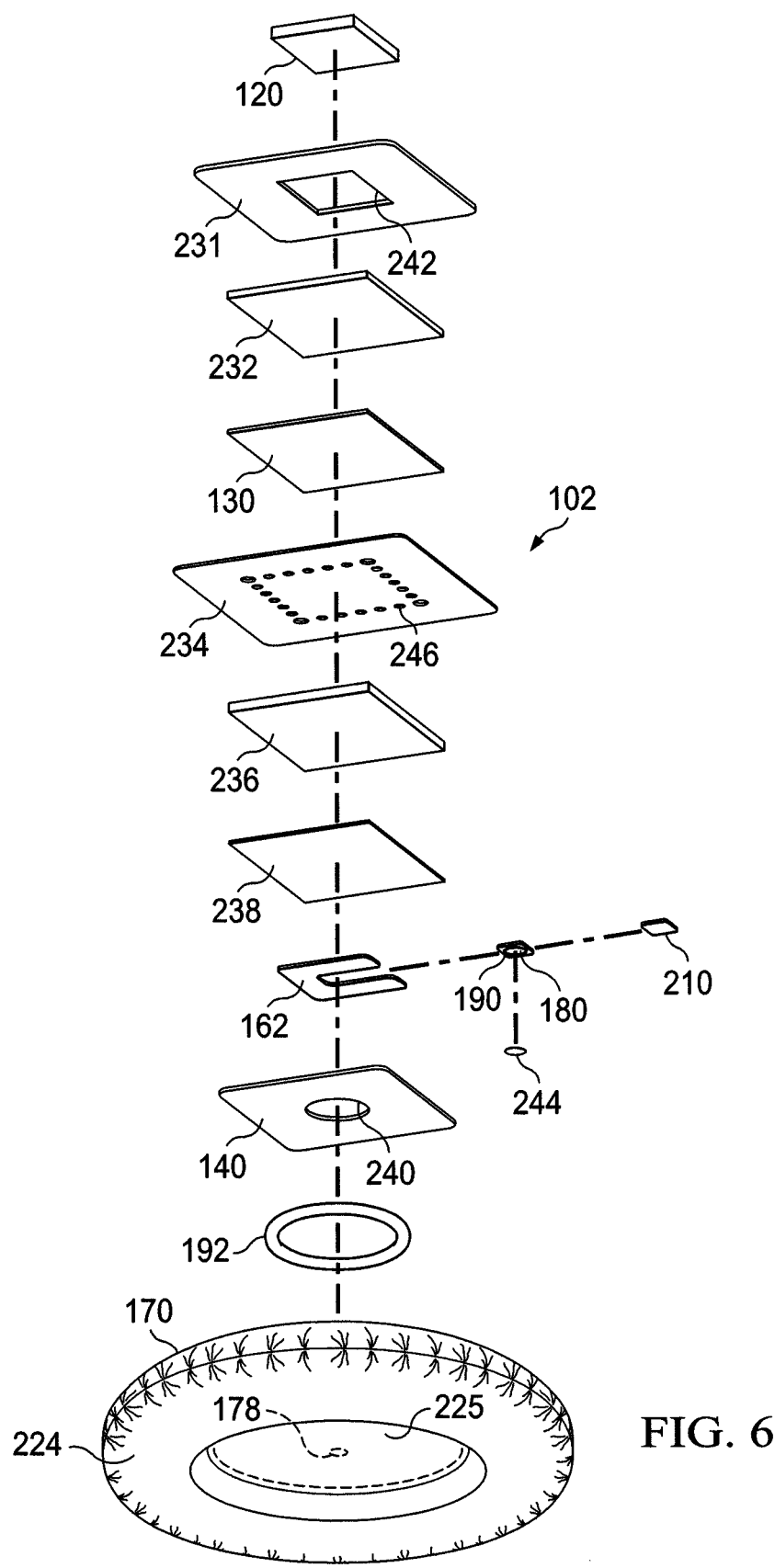
FIG. 6 is a schematic, exploded, perspective view of the reduced-pressure treatment system of FIG. 5.

Referring now primarily to FIGS. 5-6, another illustrative embodiment of a reduced pressure treatment system 100 with a dressing assembly 102 is presented. The reduced pressure treatment system 100 includes an offloading pressure component 170. In FIG. 5, which shows the offloading pressure component 170 in the inflated state, the weight or force 220 of a patient's body or body part is being supported by a surface 222, such as a bed. The offloading pressure component 170, or inflatable cushion, includes an inflatable bladder 224. With respect to a free body diagram, the weight or force 220 exerted by the patient is supported by the force 226 that is normal to and outboard of the tissue site 110 being treated. The distributed force 226 counters the force 220 without directly applying force onto the tissue site 110 itself.

The offloading pressure component 170 is shown as an inflatable annular member having the inflatable bladder 224. A central portion 225 may interface with the pump 180 to receive positive pressure exhaust from an outlet port 190. A charcoal filter 244 may be placed between the outlet port 190 and an inlet or aperture 178 of the offloading pressure component 170.

The reduced-pressure dressing assembly 102 includes a treatment manifold 120, or interface layer, adapted to be positioned at the tissue site 110, and a seal layer 231 to seal the reduced-pressure dressing assembly 102 around the tissue site 110. A first manifold layer 232 is positioned in fluid communication with the treatment manifold 120 to distribute the reduced pressure to the treatment manifold 120 and the tissue site 110. An absorbent layer 130 is positioned in fluid communication with the first manifold layer 232 to absorb liquid from at least one of the first manifold layer 232, the treatment manifold 120, and the tissue site 110. A diverter layer 234, which may contain one or more apertures 246, may be positioned adjacent to the absorbent layer 130. A second manifold layer 236 may be positioned in fluid communication with the diverter layer 234, and a liquid-air separator 238 may be positioned adjacent the second manifold layer 236. A cover 140, or drape, is positioned adjacent to the second liquid-air separator 238. An odor filter or odor-treating material may also be positioned within the reduced-pressure dressing assembly 102.

In addition to the layers of the reduced-pressure dressing assembly 102 listed above, the reduced-pressure dressing assembly 102 includes a pump 180 that may be integrated into the reduced-pressure dressing assembly 102 between the liquid-air separator 238 and the cover 140. The pump 180 may be a micropump that is small and light enough such that the reduced-pressure dressing assembly 102 (including the micropump) is able to be maintained on the tissue site 110.

The pump 180 may be disposed within the reduced-pressure dressing assembly 102 to avoid conduits and external canisters for collection of wound exudate. The pump 180 includes the outlet port 190. The outlet port 190 is in fluid communication with an aperture 240 in the cover 140. A sealing ring 192, e.g., and O-ring or seal, may be used to form a fluid seal with the outlet port 190 or to couple the offloading pressure component 170 and the reduced-pressure dressing assembly 102. Alternatively, the cover 140 may be sealed around an outlet port of the pump 180 such that gas from the pump 180 is able to exhaust directly through the aperture 240. In the embodiment illustrated in FIGS. 5-6, the outlet port 190 of the pump 180 is oriented in a direction away from the hydrophobic filter to avoid adding air under the cover 140 and to allow the air to enter the inflatable component 170, or cushion. The air exhausts through the aperture 240 in the cover 140, which may include a one-way valve. Alternatively, the air or other gas could be exhausted through a gas-permeable portion of the cover 140.

When a piezoelectric-driven pump is used as the pump 180 in the dressing assembly 102, the piezoelectric actuator associated with the pump 180 may, at times, be driven at different frequencies to act as a buzzer or vibrating alert system. The alert system may be used to alert a user to an alarm condition such as the presence of a leak in the cover 140, a change in reduced pressure as measured by a sensor, an indication that the dressing assembly 102 has absorbed a maximum capacity of liquid as may be indicated by an indicator, or an indication that one or more layers are no longer manifolding reduced pressure efficiently.

Control electronics, or control unit 210, may be utilized to control operation of the pump 180. The control unit 210 may be analog or digital and be configured with a regulator (not shown) to regulate speed or duty cycle at which the pump 180 operates. Furthermore, the control unit 210 may be configured with a controller (not shown) that receives sense signals from sensors or switches (not shown). The sensors may be disposed throughout the reduced-pressure dressing assembly 102 to sense parameters, such as pressure, temperature, moisture, chemistry, odor, or any other parameter that may be utilized in managing and controlling the pump 180. In one embodiment, the control unit 210 includes a computer processor. Alternatively, the control unit 210 may include a programmable gate array. The control unit 210 may also be formed using analog electronic components. It should be understood that the control unit 210 may include any form of digital or analog components to perform functionality as described herein.

Four parameters are often of concern when performing reduced pressure wound treatment: (i) low pressure, (ii) excessive leak, (iii) level of absorbent layer, and (iv) battery state. The control unit 210 may include electronics that may be utilized to monitor each of the four parameters and generate an alarm signal (e.g., high-pitched beep, vibration, or light) using a speaker (not shown), vibrator (not shown), or illumination device (not shown), such as a light emitting diode (LED), to notify a medical professional, patient, or family member that a parameter is outside of a safe range. For example, if a pressure at the wound site 110 is below a therapeutic level, a continuous tone may be generated. As another example, if the absorbent layer 130 is saturated, then continuous beeps may be generated. If the battery drops below a certain voltage level, then a different frequency may be generated or LED may be turned on. A variety of different alarm signals may be established to notify a medical professional or the patient to take a particular action.

An internal power source, e.g., a battery 162, may be utilized to provide electric power to the pump 180 and the control unit 210. The battery 162 may have any size and shape configuration and be housed in any material, such as polymer, to accommodate weight and size, of the reduced-pressure dressing assembly 102. In one embodiment, the battery 162 may be rechargeable. In another embodiment, the battery 162 may be disposed within or outside of the reduced-pressure dressing assembly 102 and be positioned in such a manner as to allow for easy replacement or recharging. In one embodiment, the battery 162 may be configured with a voltage level sensor (not shown) that is monitored by the control unit 210 for determination of a low power level. In one embodiment, the battery 162 may be directly connected with the pump 180. Alternatively, the battery 162 may be connected to the control unit 210 that may use power from the battery 162 to drive the pump 180. The control unit 210 may provide continuous power, modulated power, such as a pulsewidth modulated (PWM) signal, to drive the pump 180.

The seal layer 231 may be adhered to or otherwise connected to the cover 140. The seal layer 231 may include an aggressive or medical grade adhesive material that is strong enough to form a vacuum seal with skin around a wound of a patient. The seal layer 231 may be a band that has an opening 242.

In another embodiment, the seal layer 231 may be adhered to the diverter layer 234 and the diverter layer 234 adhered to the cover 140 to create an upper (or first) dressing portion and a lower (or second) dressing portion. The upper dressing portion may include the cover 140, the pump 180 and related components, the liquid-air separator 238, the second manifold layer 236, and the diverter layer 234. The lower dressing portion may include the absorbent layer 130, the first manifold layer 232, the seal layer 231, and the treatment manifold 120. In one embodiment, the reduced-pressure dressing assembly may be configured to allow replacement of the lower dressing portion once the dressing has absorbed a maximum capacity of fluid. The upper dressing portion may be reused after the lower dressing portion is replaced. This allows multiple use of the pump 180, while disposable portions of the dressing assembly 102 may be replaced. In another embodiment, the pump 180, control unit 210, and battery 162 may be removed from the dressing assembly 102 for reuse and the remaining layers of the dressing assembly 102 replaced. In still another embodiment, the absorbent layer 130 only may be replaced. In yet another embodiment, the absorbent layer 130 and the treatment manifold 120 only may be replaced.

The charcoal filter 244 may be utilized in the reduced-pressure dressing assembly 102 to reduce odors created by the tissue site and exhausted from the reduced-pressure dressing assembly 102. The charcoal filter 244 may be disposed above a valve or other output vent from the pump 180 to filter exhaust from the pump 180 prior to being released from the reduced-pressure dressing 102 into the inflatable component 170. It should be understood that the charcoal filter 244 may be alternatively configured and disposed above or below the pump 180. In another illustrative embodiment, rather than using a charcoal filter or in addition, charcoal may be integrated into any or all of the different layers utilized in the reduced-pressure dressing assembly 102.

In another illustrative embodiment, a method for collecting liquid in a dressing assembly positioned at a tissue site includes generating a reduced pressure using a pump positioned within the dressing assembly. A liquid is absorbed from the tissue site and is stored in the dressing assembly. The liquid is prevented from entering the pump. The method may further include maintaining the reduced pressure within the dressing and exhausting gas from the pump into an inflatable component that disperses forces that would otherwise be applied through the dressing assembly directly onto the tissue site.

While the depicted illustrative embodiments illustrate the use of a single pump and a single offloading pressure component, alternative embodiments may include any number of pumps and offloading pressure components. The offloading pressure component may be supplied separately so as to provide user flexibility as to when and where the offloading pressure component may be applied.

The disclosed embodiments may be used as part of a process or method for offloading pressure exerted on or near a tissue site in which reduced pressure is applied to promote healing of the tissue site and for reducing patient discomfort. In one embodiment, the method includes applying a wound dressing assembly to cover the tissue site, and applying reduced pressure to the tissue site using a reduced-pressure source coupled to the wound dressing assembly. The method further includes inflating an inner space of an offloading pressure component coupled to the reduced-pressure source. The offloading pressure component is operable to disperse positive pressure exerted on or near the tissue site for reducing the exerted pressure to the tissue site.

Although the present invention and its advantages have been disclosed in the context of certain illustrative embodiments, it should be understood that various changes, substitutions, permutations, and alterations can be made without departing from the scope of the invention as defined by the appended claims. It will be appreciated that any feature that is described in a connection to any one embodiment may also be applicable to any other embodiment.

It will be understood that the benefits and advantages described above may relate to one embodiment or may relate to several embodiments. It will further be understood that reference to "an" item refers to one or more of those items.

The steps of the methods described herein may be carried out in any suitable order, or simultaneously where appropriate.

Where appropriate, aspects of any of the embodiments described above may be combined with aspects of any of the other embodiments described to form further examples having comparable or different properties and addressing the same or different problems.

It will be understood that the above description of preferred embodiments is given by way of example only and that various modifications may be made by those skilled in the art. The above specification, examples and data provide a complete description of the structure and use of exemplary embodiments of the invention. Although various embodiments of the invention have been described above with a certain degree of particularity, or with reference to one or more individual embodiments, those skilled in the art could make numerous alterations to the disclosed embodiments without departing from the scope of the claims.

We claim:

1. A reduced-pressure treatment system for applying reduced-pressure treatment to a tissue site, the system comprising:
   a manifold adapted to be positioned proximate to the tissue site;
   a wound cover for covering the manifold and for forming a sealed space;
   a reduced-pressure source for producing a positive pressure exhaust and for providing reduced pressure to the manifold; and
   an offloading pressure component for dispersing positive pressure exerted on or near the tissue site, the offloading pressure component fluidly coupled to the reduced-pressure source external to the sealed space for receiving at least a portion of the positive pressure exhaust.

2. The reduced-pressure treatment system of claim 1, wherein the offloading pressure component is an inflatable and deflatable bladder.

3. The reduced-pressure treatment system of claim 1, wherein the offloading pressure component includes an aperture for coupling an exhaust port of the reduced-pressure source to the offloading pressure component, and wherein the positive pressure exhaust from the reduced-pressure source exits through the exhaust port and into the offloading pressure component for inflating the offloading pressure component.

4. The reduced-pressure treatment system of claim 3, further comprising an exhaust valve for limiting the flow of gas from the exhaust port into the offloading pressure component.

5. The reduced-pressure treatment system of claim 3, further comprising a sealing ring operable to maintain a seal between the exhaust port of the reduced-pressure source and the offloading pressure component.

6. The reduced-pressure treatment system of claim 1, wherein the offloading pressure component includes a relief valve operable to release air from the offloading pressure component.

7. The reduced-pressure treatment system of claim 1, wherein the reduced-pressure source includes a reduced-pressure valve that enables the reduced-pressure source to draw atmospheric air into the offloading pressure component to inflate the offloading pressure component.

8. The reduced-pressure treatment system of claim 1, wherein the offloading pressure component comprises at least two layers of flexible film welded together.

9. A system for treating a tissue site with reduced pressure, the system comprising:
   a reduced-pressure source that produces reduced pressure and a positive pressure exhaust;
   a manifold configured to be fluidly coupled to the reduced-pressure source to receive the reduced pressure; and
   an offloading pressure component having a deflated state and an inflated state, the offloading pressure component comprising at least one flexible wall forming an inner space of the offloading pressure component, the inner space adapted to be fluidly coupled to the reduced-pressure source and operable to receive the positive pressure exhaust generated by the reduced-pressure source.

10. The system of claim 9, wherein the inner space is fluidly coupled to an exhaust port of the reduced-pressure source to receive positive pressure exhaust.

11. The system of claim 9, wherein the inner space is formed by two layers of flexible film welded together.

12. The system of claim 9, wherein the inner space is formed by two layers of flexible film adhesively bonded together.

13. The system of claim 1, further comprising:
   an aperture located on one of the two layers for coupling an exhaust port of the reduced-pressure source to the offloading pressure component.

14. The system of claim 11, further comprising:
   an aperture located on one of the two layers for coupling an exhaust port of the reduced-pressure source to the offloading pressure component; and
   a sealing ring operable to maintain a seal between the exhaust port of the reduced-pressure source and the offloading pressure component.

15. The system of claim 9, further comprising a relief valve operable to release air from the offloading pressure component.

16. The system of claim 9, further comprising a pressure sensor for determining a pressure within the inner space.

17. The system of claim 9, wherein the inner space forms a donut shape.

18. A method for offloading pressure exerted proximate to a tissue site in which reduced pressure is applied, the method comprising:
   applying a manifold proximate to the tissue site;
   applying a wound cover over the manifold;
   applying reduced pressure to the manifold using a reduced-pressure source coupled to the wound cover; and
   inflating an inner space of an offloading pressure component with a positive-pressure exhaust from the reduced-pressure source, the offloading pressure component operable to disperse positive pressure exerted proximate to the tissue site.

19. The method of claim 18, wherein the reduced-pressure source is a micropump.

20. The method of claim 18, further comprising inflating the inner space of the offloading pressure component using gas generated by the reduced-pressure source.

21. The method of claim 18, further comprising inflating the inner space of the offloading pressure component using exhaust generated by the reduced-pressure source while the reduced-pressure source is supplying reduced pressure to the tissue site.

22. The method of claim 18, further comprising limiting inflation of the inner space of the offloading pressure component using an exhaust valve.

23. The method of claim 18, further comprising:
   monitoring a pressure within the offloading pressure component using at least one sensor; and
   triggering an alarm in response to the pressure exceeding a threshold.

24. The method of claim 18, further comprising applying a sealing ring between an exhaust port of the reduced-pressure source and the offloading pressure component in order to couple the exhaust port of the reduced-pressure source to an inner space of the offloading pressure component.

25. The method of claim 18, further comprising powering the reduced-pressure source using a power source integrated within the wound cover.

26. The method of claim 18, further comprising powering the reduced-pressure source using an external power source.

* * * * *